US00PP26253P2

(12) United States Plant Patent
Arts

(10) Patent No.: US PP26,253 P2
(45) Date of Patent: Dec. 22, 2015

(54) POINSETTIA PLANT NAMED 'BKPONSL'

(50) Latin Name: ***Euphorbia pulcherrima* Willd.**
Varietal Denomination: Bkponsl

(71) Applicant: Niels Arts, De Kwakel (NL)

(72) Inventor: Niels Arts, De Kwakel (NL)

(73) Assignee: Beekenkamp Plants B.V., Massdijk (NL)

( * ) Notice: Subject to any disclaimer, the term of this patent is extended or adjusted under 35 U.S.C. 154(b) by 25 days.

(21) Appl. No.: 14/120,116

(22) Filed: Apr. 25, 2014

(51) Int. Cl.
*A01H 5/02* (2006.01)

(52) U.S. Cl.
USPC ..... Plt./307

(58) Field of Classification Search
USPC ..... Plt./307
CPC ..... A01H 5/0244; A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of Poinsettia plant named 'Bkponsl', characterized by its upright and uniformly mounding plant habit; vigorous growth habit; freely branching habit; dark green-colored leaves; large and full inflorescences with dark red-colored flower bracts; and excellent post-production longevity.

2 Drawing Sheets

Botanical designation: *Euphorbia pulcherrima* Willd.
Cultivar denomination: 'BKPONSL'.

BACKGROUND OF THE INVENTION

The present invention relates to a new and distinct, cultivar of Poinsettia plant, botanically known as *Euphorbia pulcherrima* Willd. and hereinafter referred to by the name 'Bkponsl'.

The new Poinsettia plant is a product of a planned breeding program conducted by the Inventor in De Kwakel, The Netherlands. The objective of the breeding program is to create uniform and freely-branching Poinsettia plants with low temperature tolerance and good postproduction longevity.

The new Poinsettia plant originated from a cross-pollination made by the Inventor in December, 2007 in De Kwakel, The Netherlands of a proprietary selection of *Euphorbia pulcherrima* Willd. identified as code number 99-0017-000, not patented, as the female, or seed, parent with a proprietary selection of *Euphorbia pulcherrima* Willd. identified as code number 99-0034-000, not patented, as the male, or pollen, parent. The new Poinsettia plant was discovered and selected by the Inventor as a single flowering plant within the progeny of the stated cross-pollination in a controlled greenhouse environment in De Kwakel, The Netherlands in December, 2008.

Asexual reproduction of the new Poinsettia plant by terminal vegetative cuttings in a controlled greenhouse environment in De Kwakel, The Netherlands since February, 2009 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bkponsl'. These characteristics in combination distinguish 'Bkponsl' as a new and distinct Poinsettia plant:

1. Upright and uniformly mounding plant habit.
2. Vigorous growth habit.
3. Freely branching habit.
4. Dark green-colored leaves.
5. Large and full inflorescences with dark red-colored flower bracts.
6. Excellent post-production longevity.

Plants of the new Poinsettia can be compared to plants of the female parent selection. Plants of the new Poinsettia differ primarily from plants of the female parent selection in the following characteristics:

1. Plants of the new Poinsettia are more freely branching than plants of the female parent selection.
2. Plants of the new Poinsettia have darker green-colored leaves than plants of the female parent selection.

Plants of the new Poinsettia can be compared to plants of the male parent selection. Plants of the new Poinsettia differ primarily from plants of the male parent selection in the following characteristics:

1. Plants of the new Poinsettia are more freely branching than plants of the male parent selection.
2. Plants of the new Poinsettia have longer postproduction longevity than plants of the male parent selection.

Plants of the new Poinsettia can be compared to plants of *Euphorbia pulcherrima* Willd. 'Floasatur', disclosed in U.S. Plant Pat. No. 20,230. In side-by-side comparisons conducted in De Kwakel, The Netherlands, plants of the new Poinsettia differed primarily from plants of 'Floasatur' in the following characteristics:

1. Plants of the new Poinsettia were larger than plants of 'Floasatur'.

2. Plants of the new Poinsettia grew slightly slower than plants of 'Floasatur'.
3. Plants of the new Poinsettia were more freely branching than plants of 'Floasatur'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet comprises a side perspective view of a typical flowering plant of 'Bkponsl' grown in a container.

The photograph on the second sheet is a close-up view of the upper and lower surfaces of typical inflorescences and leaves of 'Bkponsl'.

DETAILED BOTANICAL DESCRIPTION

The aforementioned photographs and following observations and measurements describe plants grown during the autumn and winter in 13-cm containers in a glass-covered greenhouse in De Kwakel, The Netherlands and under cultural practices typical of commercial Poinsettia production. During the first ten weeks of production of the plants, day and night temperatures averaged 20° C. During the last weeks of production of the plants, day and night temperatures averaged 17° C. Throughout the entire production of the plants, the light level averaged 200 Watts/m$^2$. Plants were pinched one time and were 18 weeks old when the photographs and the detailed description were taken. In the following description, color references are made to The Royal Horticultural Society Colour Chart, 2007 Edition, except where general terms of ordinary dictionary significance are used.

Botanical classification: *Euphorbia pulcherrima* Willd. 'Bkponsl'.

Parentage:

*Female, or seed, parent*.—Proprietary selection of *Euphorbia pulcherrima* Willd. identified as code number 99-0017-000, not patented.

*Male, or pollen, parent*.—Proprietary seedling selection of *Euphorbia pulcherrima* Willd. identified as code number 99-0034-000, not patented.

Propagation:

*Type*.—Terminal vegetative cuttings.

*Time to initiate roots, summer*.—About ten days at temperatures about 22° C.

*Time to initiate roots, winter*.—About two weeks at temperatures about 22° C.

*Time to produce a rooted young plant, summer and winter*.—About four weeks at temperatures about 22° C.

*Root description*.—Medium in thickness to thick, fibrous; white in color.

*Rooting habit*.—Freely branching; medium density.

Plant description:

*Plant and growth habit*.—Upright and uniformly mounded plant habit; inverted triangle with rounded crown; large full inflorescences positioned above the foliar plane; vigorous growth habit and moderate growth rate.

*Plant height*.—About 25 cm.

*Plant diameter or spread*.—About 30 cm.

*Lateral branch description*.—Branching habit: Freely branching habit, about six lateral branches develop after pinching. Length: About 18 cm to 20 cm. Diameter: Thick, about 5 mm. Internode length: About 1 cm to 1.3 cm. Strength: Strong. Texture: Smooth, glabrous. Angle: Mostly upright. Color: Close to 144A.

*Leaf description*.—Arrangement: Alternate, simple. Length: About 9 cm to 12 cm. Width: About 7 cm to 8 cm. Shape: Roughly ovate. Apex: Acuminate. Base: Obtuse to slightly cordate. Margin: Entire, shallowly lobed. Venation pattern: Pinnate. Texture, upper and lower surfaces: Smooth, glabrous. Color: Developing leaves, upper surface: Close to 139B. Developing leaves, lower surface: Close to 141D. Fully expanded leaves, upper surface: Close to 139A; venation, close to 147A. Fully expanded leaves, lower surface: Close to 141C, venation, close to 139C. Petiole: Length: About 5 cm to 6 cm. Diameter: About 3 mm. Texture, upper and lower surfaces: Smooth, glabrous. Color, upper and lower surfaces: Close to 183B.

Inflorescence description:

*Inflorescence type and habit*.—Large full inflorescences are compound corymbs of cyathia with dark red-colored flower bracts subtending the cyathia; one inflorescence per lateral branch with inflorescences positioned above and beyond the foliar plane.

*Fragrance*.—None detected.

*Natural flowering season*.—Plants flower naturally during the winter under long nyctoperiod conditions; inflorescence initiation and development can be induced under artificial long nyctoperiod conditions; early flowering habit, response time is about eight weeks.

*Post-production longevity*.—Excellent post-production longevity; plants of the new Poinsettia maintain good substance and bract color for about six weeks under interior conditions; flower bracts persistent.

*Inflorescence diameter*.—About 18 cm to 20 cm.

*Inflorescence height*.—About 5 cm.

*Flower bracts*.—Quantity per inflorescence: About 13 to 15. Length: About 10 cm. Width: About 6.5 cm. Shape: Ovate. Apex: Acute to acuminate. Base: Obtuse to cordate. Margin: Entire, lobed. Venation: Pinnate. Texture, upper surface: Slightly rugose, glabrous. Texture, lower surface: Smooth, glabrous. Aspect: Mostly flat. Color: Developing bracts, upper surface: Close to 187B with random green-colored sectors. Developing bracts, lower surface: Close to 147B with random red-colored sectors. Fully expanded bracts, upper surface: Close to 53B; venation, close to 53B; color does not fade with development. Fully expanded bracts, lower surface: Close to 46C; venation, close to 46C; color does not fade with development. Bract petioles: Length: About 2 cm. Diameter: About 2 mm. Texture, upper and lower surfaces: Smooth, glabrous. Color, upper surface: Close to 187C. Color, lower surface: Close to 181C.

*Cyathia*.—Quantity per corymb: About seven. Length: About 1 cm. Width: About 5 mm. Shape: Ovoid. Color, developing, inner and outer surfaces: Close to 144A. Color, fully developed, inner and outer surfaces: Close to 144B. Nectaries: Quantity per cyathium: Typically one or two. Length: About 6 mm. Diameter: About 2 mm. Shape: Elliptical. Texture, inner and outer surfaces: Smooth, glabrous. Color, developing, inner and outer surfaces: Close to 150B. Color, fully developed, inner and outer surfaces: Close to 15C.

*Peduncles*.—Length: About 5 mm to 10 mm. Diameter: About 5 mm. Strength: Strong. Texture: Smooth, glabrous. Angle: Mostly upright. Color: Close to 146A blushed with red.

*Reproductive organs*.—Stamens: Quantity per cyathium: About eight to ten. Filament length: About 2 mm. Filament color: Close to 185B. Anther shape: Oval. Anther length: About 5 mm. Anther color: Close to 6B. Amount of pollen: Abundant. Pollen color: Close to 15B. Pistils: Quantity per cyathium: Typically one. Pistil length: About 3 mm. Style length: About 3 mm. Style color: Close to 46B. Stigma shape: Oval, six-lobed. Stigma color: Close to 46B. Ovary color: Close to 143A. Seeds and fruits: Seed and fruit production has not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate high temperature about 35° C. and to be hardy to USDA Hardiness Zone 10.

It is claimed:

1. A new and distinct Poinsettia plant named 'Bkponsl' as illustrated and described.

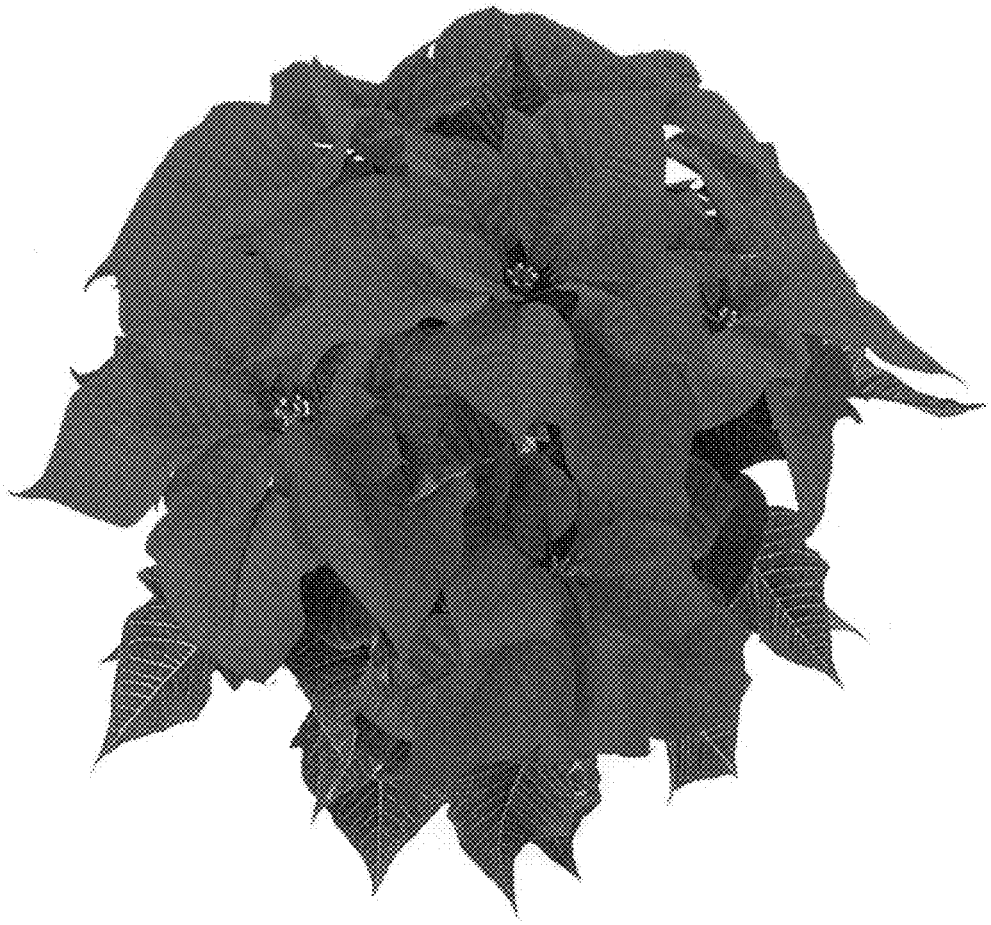

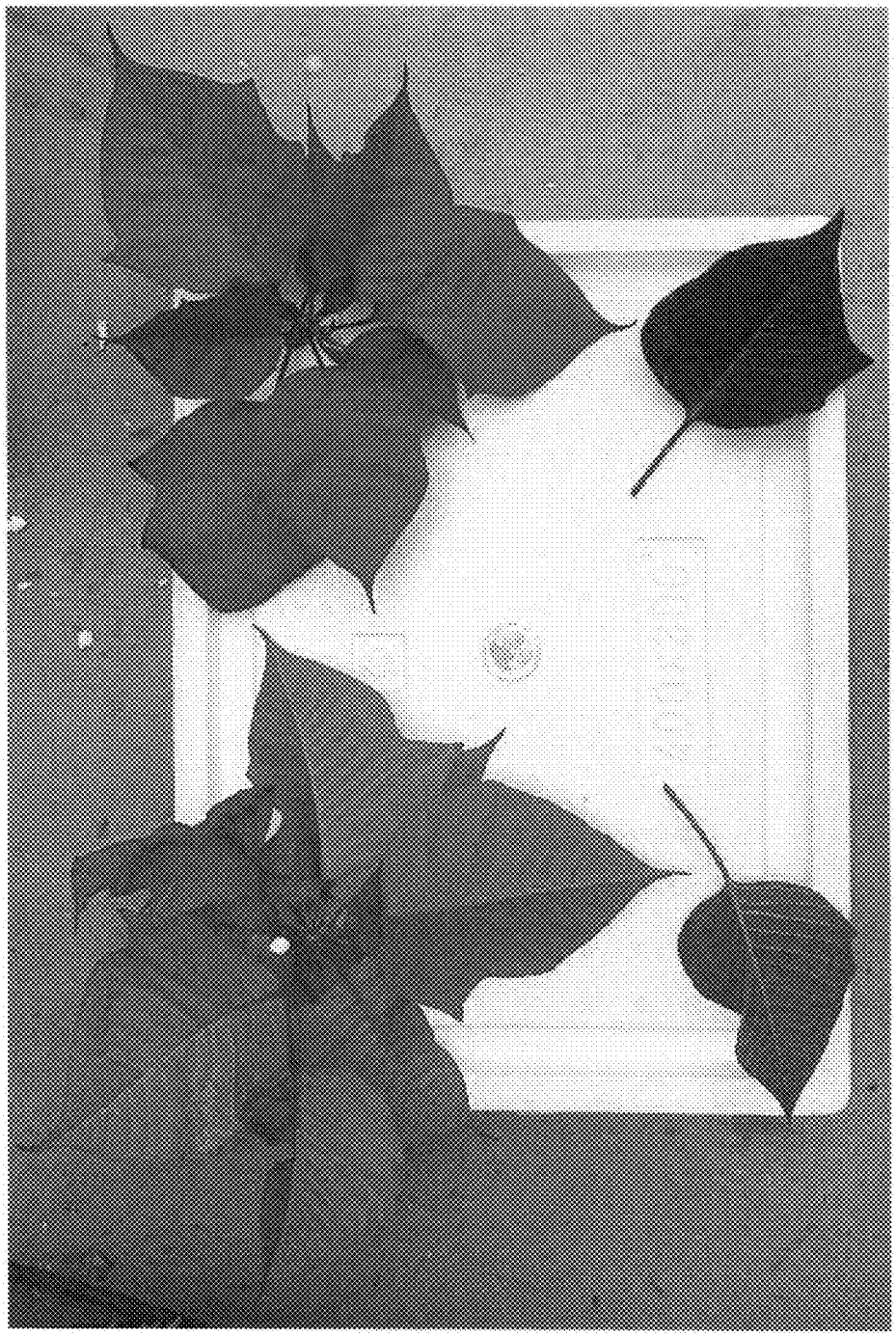

* * * * *